United States Patent [19]
Cochrum

[11] Patent Number: 6,001,387
[45] Date of Patent: Dec. 14, 1999

[54] SPIN DISK ENCAPSULATION APPARATUS AND METHOD OF USE

[75] Inventor: Kent C. Cochrum, Davis, Calif.

[73] Assignee: The Reguents of the University of California, Oakland, Calif.

[*] Notice: This patent is subject to a terminal disclaimer.

[21] Appl. No.: 08/886,266

[22] Filed: Jul. 1, 1997

Related U.S. Application Data

[63] Continuation-in-part of application No. 08/237,290, May 3, 1994, Pat. No. 5,643,594, which is a continuation-in-part of application No. 07/891,564, May 29, 1992, Pat. No. 5,429, 821, and a continuation-in-part of application No. 08/186, 327, Jan. 24, 1994, Pat. No. 5,578,314, and a continuation-in-part of application No. 08/185,709, Jan. 24, 1994, Pat. No. 5,521,079.

[51] Int. Cl.[6] .................. A61F 2/02; A01N 1/02; C12N 11/02; B39C 39/10

[52] U.S. Cl. .................. 424/424; 635/178; 635/179; 635/180; 635/182; 264/4; 264/7; 264/8

[58] Field of Search ............................ 424/424; 435/178, 435/179, 180, 182; 264/4, 7, 8

[56] References Cited

U.S. PATENT DOCUMENTS

| | | | |
|---|---|---|---|
| 2,955,956 | 10/1960 | Baugh, et al. | 117/100 |
| 3,429,295 | 2/1969 | Shapiro | 118/49.1 |
| 3,870,014 | 3/1975 | Buck | 118/52 |
| 4,298,476 | 11/1981 | Dudley | 210/373 |
| 4,318,941 | 3/1982 | Gillett et al. | 427/212 |
| 4,352,883 | 10/1982 | Lim | 435/178 |
| 4,386,895 | 6/1983 | Sodickson | 425/5 |
| 4,391,909 | 7/1983 | Lim | 435/178 |
| 4,407,957 | 10/1983 | Lim | 435/178 |
| 4,409,331 | 10/1983 | Lim | 435/178 |
| 4,663,286 | 5/1987 | Tsang | 435/178 |
| 4,673,566 | 6/1987 | Goosen et al. | 424/19 |
| 4,675,140 | 6/1987 | Sparks et al. | 264/4.3 |
| 4,689,293 | 8/1987 | Goosen et al. | 435/1 |
| 4,749,620 | 6/1988 | Rha et al. | 428/402.2 |
| 4,800,160 | 1/1989 | Iguchi et al. | 435/177 |
| 4,803,168 | 2/1989 | Jarvis, Jr. | 435/240 |
| 4,806,355 | 2/1989 | Goosen et al. | 424/424 |
| 4,902,295 | 2/1990 | Walthall et al. | 623/11 |
| 4,997,443 | 3/1991 | Walthall et al. | 623/11 |
| 5,061,520 | 10/1991 | Hermelin | 427/212 |
| 5,643,594 | 7/1997 | Dorian et al. | 424/424 |

Primary Examiner—Carlos A. Azpuru
Attorney, Agent, or Firm—Hana Verny

[57] ABSTRACT

An encapsulating apparatus comprising a spinning cup adjustably rotatable about its central axis for forming droplets and projecting them radially outward, and one or more collection basins surrounding the bead forming spinning cup independently rotatable and positioned to collect the beads projected from the cup. The method for forming tissue microcapsules using the spin disk encapsulation apparatus wherein a supply mixture is introduced into a mixing chamber of the cup from a single, multiple or concentric needles. As the cup spins, the coated particles are propelled upward by the centrifugal force from the mixing chamber along the inner surface of the cup, projected radially outward, as beads, into the gelling solution in one of the selected basins.

19 Claims, 7 Drawing Sheets

SPIN DISK ENCAPSULATION APPARATUS AND METHOD OF USE

CROSS-REFERENCE TO RELATED APPLICATIONS

This is a continuation-in-part of the application Ser. No. 08/237,290, for "Spin Encapsulation Apparatus and Method of Use", filed May 3, 1994, to be issued as U.S. Pat. No. 5,643,594, on Jul. 1, 1997, which is a continuation-in-part of application Ser. No. 07/891,564, for "Non-fibrogenic High Mannuronate Alginate Coated Transplants, Processes for their Manufacture, and Methods for their Use", filed May 29, 1992, now U.S. Pat. No. 5,429,821, issued on Jul. 4, 1995, and application Ser. No. 08/186,327, for "Multiple Layer Alginate Coatings of Biological Tissue for Transplantation", filed Jan. 24, 1994, now U.S. Pat. No. 5,578,314, issued on Nov. 26, 1996, all of which are incorporated herein by reference. This application is also a continuation in part of application Ser. No. 08/185,709, for "Microcapsule Generating System Containing an Air Knife and Method of Encapsulating", filed Jan. 24, 1994, now U.S. Pat. No. 5,521,079, issued on May 28, 1996, which is incorporated herein by reference.

BACKGROUND OF THE INVENTION

1. Field of the Invention

The present invention concern a spin disk apparatus and a method of use od said apparatus for coating biological materials such as tissues, cells and cell lines with a continuous, uniform, semi-permeable and bio-compatible coating. More particularly, this invention relates to a spin encapsulation apparatus and method for providing continuous uniform coatings of the biological material and other solid and semi-solid particles, to form smooth and uniform size microcapsules.

The apparatus comprises a particle suspension supply system, consisting of a container connected to a one or more centrally or off-center positioned needles and/or two or more concentrical needles positioned centrally or off-center, for storing the particles to be encapsulated in a coating polymer solution. The suspension supply system allows accurate metering of a suspension comprising particles to be coated and a coating polymer and introduction of the suspension onto the wall of a spinning beads forming cup of the spinning apparatus. The spinning apparatus further comprises a cup or disk for forming suspension droplets and projecting them outward from its central axis and into a collecting basin containing a gelling solution. The collecting basin surrounds the beads forming cup and is mounted for rotation about its central axis and positioned to collect droplets projected outward from the bead forming cup. The droplet forming cup and the collecting basin are independently connected to individual rotational motor drives having adjustable speeds. The needles of the supply system are positioned manually or, optionally, a conductivity data acquisition program/digital gauging probe system is used to determine and set the distance between dispensing needles and surface of bead forming cup.

2. Background Art and Related Art Disclosures

Coating or microencapsulation of solid particles in general, and biological materials in particular, is widely employed to protect the encapsulated substances from environmental effects, to control their release time, and to confer improved handling characteristics. Typical substances which are coated or microencapsulated are drugs and biological materials such as tissues, cells and cell lines.

Attempts to transplant organ tissues into genetically dissimilar hosts without immunosuppression have been generally defeated by the immune system of the host. The application of effective protective barrier coatings to isolate the transplant tissues from the host immune system has not proven to be medically practical for a number of reasons. The coating materials were incompatible with the host system or unsuitable for other reasons. Encapsulation or coating processes and apparatuses previously developed did not yield reproducible coatings having the desired permeability and thickness required for the transplant tissue to have a long and effective functioning life in the host.

To protect transplants from destruction by the immune response of the host animal, various attempts have been made to create a protective barrier between the transplant tissue or cells and the immunological components of the host's system. T. M. S. Chang, *Science* 146: 524–525 (1964) described the microencapsulation of erythrocyte hemolysate and urease in semi-permeable polyamide membranes. These microcapsules did not survive for long when injected into the blood stream. K. Mosbach et al, *Acta Chem.Scand.* 20:2807–2812 (1966) and T. M. S. Chang et al, *Can.J-.Physiol. and Pharmacology* 44: 115–128 (1966) described the preparation of semi-permeable microencapsulated microbial cells and viable red blood cells, the latter article mentioning the possibility of using injections of encapsulated cells for organ replacement therapy.

Numerous other conventional coating or microencapsulation techniques have been developed. By and large, these techniques suffer from the inability to precisely control the thickness of the coating and the overall diameter of the microcapsules, while maintaining the ability to efficiently generate one or multiple coatings with smooth outer surfaces. The following patents exemplify these conventional techniques: U.S. Pat. No. 4,386,895 to Sodickson, U.S. Pat. No. 4,675,140 to Sparks et al., and U.S. Pat. No. 4,800,160 to Iguchi et al., and are hereby incorporated by reference.

The Sodickson patent discloses a capsule forming apparatus having an elaborate design of reservoirs and conduits. The capsule forming apparatus includes a rotor assembly which defines a gelling agent reservoir, and a rotor having a central axis of rotation. The rotor assembly is connected to a motor and a drive shaft. When the motor is actuated, the rotor assembly rotates about its axis. The rotor consists of a disc-shaped block having four radial vanes, and defines two concentric circular reservoirs and an opening coaxial to the rotor axis. A pair of conduits are spaced apart by 180 degrees adjacent to the bottom of the reservoir, for communication with two radial tubes. The reservoir and its associated conduits serve to replenish the gelling agent during the production of microcapsules.

Several radial conduits are disposed near the bottom of the reservoir, and communicate with a bundle of radial hollow needles. Four ducts are disposed next to the central opening and communicate with microcapsule-collecting tubes, and with yet another reservoir. The rotor assembly includes a vertical sidewall 68. In operation, the gelling agent is placed in the reservoir and a suspension is placed in the reservoir. When the rotor assembly is caused to rotate, the liquid gelling agent in the reservoir is centrifugally urged to form a layer 15–25 mm thick on the sidewall. Simultaneously, the gellable liquid and core material in the reservoir are centrifugally urged through the conduits and needles. As the liquid passes out of the needles, it breaks up into droplets which are propelled radially across a 2–5 mm gap to the layer of gelling agent, where they are gelled.

The Sparks et al. patent describes another method of coating particles by feeding a suspension of two materials onto a rotating disc. The suspension is centrifugally dispersed by the rotating disc into relatively small droplets of coating material. As the coated particles are dispersed by the rotating disc, they are solidified by exposure to air, and are separated by sieving. FIGS. 13–15 of the patent illustrate various conical and cup shaped forms of the rotary disc.

The Iguchi et al. patent describes a process and apparatus for producing immobilized enzyme granules, by forming drops of a gellable enzyme-containing liquid with a rotating disc, and bringing the drops in contact with a gelling solution. The disc is contained in a column, and the gelling solution flows down the walls of the column to a reservoir. Drops of the enzyme-containing liquid from the rotating disc contact the gelling solution while flowing down the walls and are carried to the reservoir.

Other encapsulation methods have comprised a procedure for forming droplets of the encapsulating medium and the biological material and a procedure for solidifying the encapsulating medium. Agarose encapsulated materials have been formed by chilling an emulsion of agarose droplets containing biological materials as shown by Nilsson et al, *Nature* 302:629–630 (1983) and Nilsson et al., *Eur. J. Appl. Microbiol. Biotechnol.* 17:319–326 (1983). Injection of droplets of polymer containing biological materials into a body of coolant such as a concurrently liquid stream has been reported by Gin et al, *J.Microencapsulation* 4:329–242 (1987).

Alginates form a gel when reacted with calcium ions. Alginate droplets have been formed by emulsifying a solution of sodium alginate containing cellular material to form droplets of sodium alginate and cells, and gelling the droplets with calcium chloride in U.S. Pat. No. 4,352,883. Alginate droplets have also been formed with a syringe and pump to force droplets from a needle, using a laminar flow air knife to separate droplets from the tip, the droplets being gelled by collecting them in a calcium chloride solution in U.S. Pat. No. 4,407,957. Alginate droplets have also been formed by the simple procedure of expelling them from a hypodermic needle and allowing the droplets to fall into a calcium chloride solution, as described by Nigam et al, *Biotechnology Techniques* 2:271–276 (1988).

Droplets have also been injected into a concurrently flowing stream containing calcium chloride in U.S. Pat. No. 3,962,383. Spraying alginate solutions through a spray nozzle to form a mist of droplets which were collected in a calcium chloride solution was reported by Plunkett et al, *Laboratory Investigation* 62:510–517 (1990). These methods have not proven effective for mass production of coatings having properties required for successful transplantation.

Hommel et al. in U.S. Pat. No. 4,789,550 disclose the formation of alginate droplets using a combination of a needle and a square wave electrical electrostatic voltage to form uniform droplets. The alginate solution is forced from the tip of a needle to form a droplet, and the droplet is pulled from the needle by a changing electrostatic field between the needle tip and a calcium chloride solution placed below the needle tip. The droplet receives a charge of one polarity from the needle, opposite to the charge in the calcium chloride solution. When the voltage difference between the droplet and the oppositely charged calcium chloride solution reaches a value at which the attraction by the solution on the droplet exceeded the force of interfacial tension holding the droplet on the needle tip, the droplet is pulled free to fall into the calcium chloride solution. The electrostatic field is fluctuated using a square wave form to create a succession of voltages crossing the threshold voltage at which droplets are pulled free from the needle, thus producing a continuous series of droplets, one per square wave cycle. The process is not found to provide the small droplets and thin coatings required for effective transplantation.

None of the above described art results in formation of microcapsules which have a small but uniform size, uniform thickness of coating and which does not produce substantial number of empty spheres.

Thus, there is still an unsatisfied need for new methods of preparing tissue transplants having properties needed for long-term survival of these transplants in human or animal body. There is, therefore, also a need for an encapsulation apparatus which efficiently produces transplants of the tissue coated with a single or multiple coatings with a high degree of size and thickness of coating control and reproducibility, at a rate to satisfy demands for transplant quantities.

All patents, patent applications and publications cited herein are hereby incorporated by reference.

SUMMARY

It is therefore one object of the present invention to provide an improved spin disk encapsulation apparatus for coating biological materials such as tissues, cells and cell lines with a continuous, uniform, 20–200 micron thick, semi-permeable and bio-compatible coating.

Another object of the present invention is to provide an improved spin disk apparatus which comprises a particle suspension supply system comprising a container connected to a one or more centrally or off-center positioned needles and/or to two or more concentrical needles positioned centrally or off-center, for storing the particles to be encapsulated in a coating polymer solution, said suspension supply system allowing accurate metering of a suspension comprising particles to be coated and a coating polymer and introducing said suspension onto the wall of a spinning beads forming cup of the spinning apparatus, said spinning apparatus further comprising a cup or disk for forming suspension droplets and projecting them outward from its central axis and into a collecting basin containing a gelling solution, said collecting basin surrounding the beads forming cup and mounted for rotation about its central axis and positioned to collect droplets projected outward from the bead forming cup, said droplet forming cup and the collecting basin being independently connected to individual rotational motor drives having adjustable speeds. The needles of the suspension supply system are positioned manually or, optionally, a conductivity data acquisition program/digital gauging probe system is used to determine and set the distance between dispensing needles and surface of bead forming cup.

It is still another object of the present invention to provide a spin disk encapsulation method for manufacturing thin, uniform, continuous coatings of biological tissues, cells, cell lines and other solid and semi-solid biological and non-biological particles, which results in the microcapsules being 20–200 microns in size, producing such microcapsules with a high degree of size control, at a rapid rate to enable mass production, which allows precise control of coating thickness and overall diameter of the coated microcapsules, which decreases the number or eliminates the formation of blank spheres, which allows efficient generation of one or multiple coatings with smooth outer surfaces.

It is still yet another object of the present invention to provide a spin disk encapsulation method for producing coated pancreatic islet cells transplant producing insulin for transplantation into diabetic patients.

It is yet another object of the present invention to provide a spin disk encapsulation apparatus and method which minimize the impact of the beads formed on the beads forming surface of the spinning cup as they are propelled and captured in a gelling solution and thus prevent the transplant's tissue destruction or damage.

It is still another object of the present invention to provide variations of the improved spin disk encapsulation apparatus comprising a spinning cup for forming droplets and projecting them radially outward, and a plurality of axially adjacent collecting basins of different sizes which are of the same size or sizes which gradually increase from bottom to top, wherein each collecting basin includes a gelation chamber for receiving the capture solution upon rotation, and a collecting chamber for receiving the capsules when the collecting basin is not rotating.

DEFINITIONS

Figure 1:
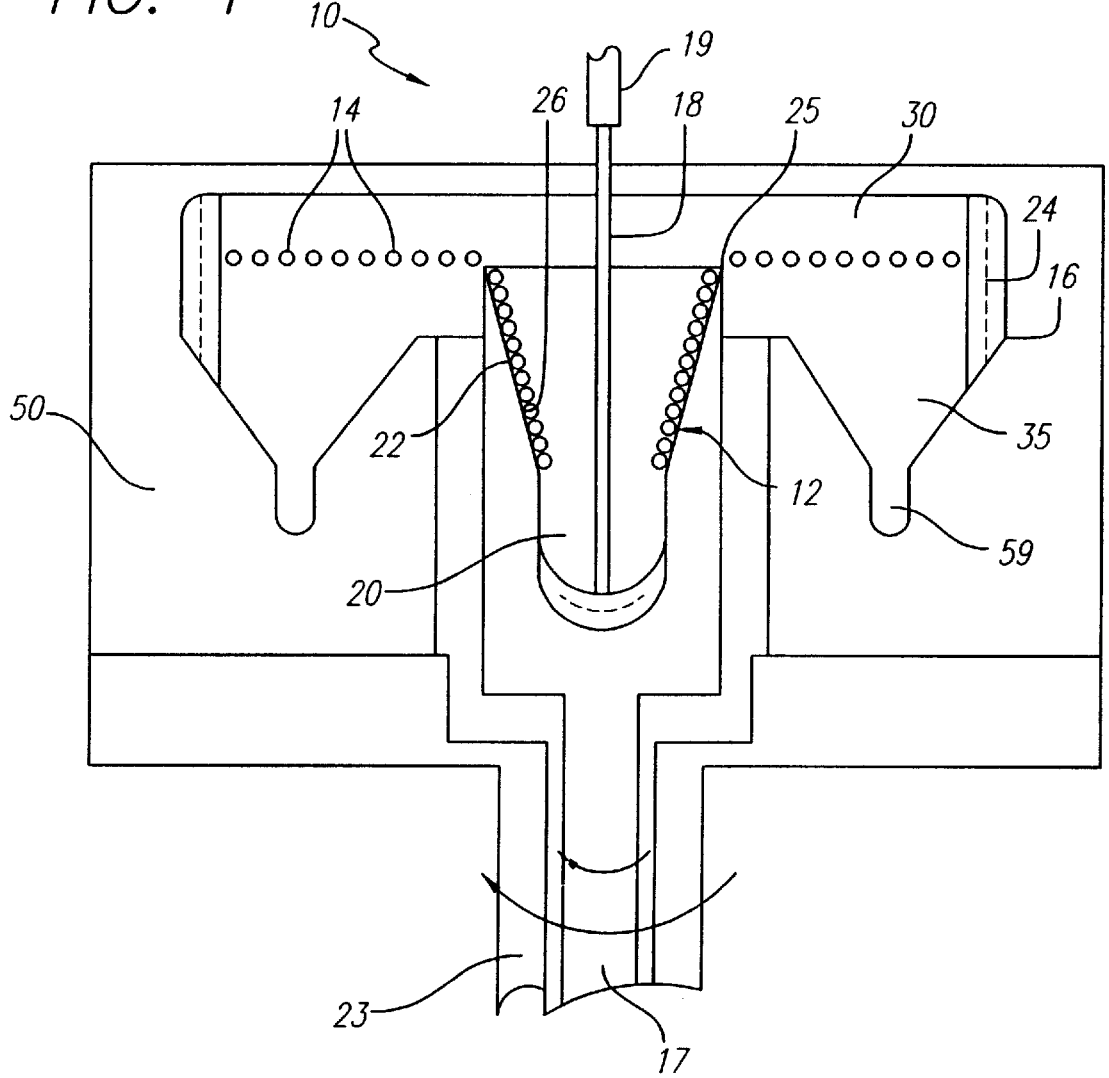
FIG. 1 is a schematic side elevational view of a simplified spin disk encapsulation apparatus shown in operation, and which is provided to perform an encapsulation process according to the present invention.

As used herein, the term:

"Transplant", "particle", "tissue" or "biological material" means and includes all living tissues, cells and cell lines, and biologically active substances intended to be implanted into the body of a host animal and the act of implanting these tissues, cells and cell lines. These tissues, cells and cell lines include, without limitation, tissue and cells removed from a donor animal, tissues, cells and cell lines obtained by incubation or cultivation of donor tissues and cells, cells obtained from viable cell lines, biologically active products of cells and tissues, and the like.

"Bead" means a bead formed by spinning of the suspension of the tissue and polymer introduced on the wall of the spinning disk through the suspension supply system.

"Supply mixture" means a suspension of tissue or particles in a polymer, such as alginate or agarose.

"Allograft" means a graft transplanted between genetically nonidentical individuals of the same species.

"Xenograft" means a graft transplanted from an animal of one species to one of another species.

"Spinning disk", "spinning disk cup", "bead forming disk" or "bead forming cup" are used interchangeably to describe a chamber where the coated particles are formed during spinning.

DETAILED DESCRIPTION OF THE INVENTION

The present invention provides an improved spinning disk apparatus to be used in a method for coating biological materials such as tissues, cells, cell lines, allograft or xenograft, with a continuous, uniform thickness, thin, semipermeable and bio-compatible coating.

Apparatus improved according to the invention contains centrally or off-center positioned one or plurality of needles or plurality of concentrical needles allowing a mass production of small coated microcapsules containing the biological tissue at a high rate without producing at the same time a large number of blank spheres not containing tissue or cells.

The apparatus improvement is based on the concentricity and/or off-center positioning of the needles of the supply mixture system, which needles are further positioned closely to the side of the spinning cup in such a way that the suspension of the tissue and polymer flows on the side of the spinning disk and only there the beads are formed. Although it is also possible to introduce the supply suspension in the form of drops, for the production of small and thinly coated transplant microcapsules, the supply suspension is preferably introduced as a flow stream.

The apparatus further comprises a spinning disk having a shape of a cup for converting, during spinning and rotation, the supply suspension stream into individual beads comprising the tissue surrounded by the polymer and by a spinning centrifugal force projecting these beads outward from its central axis and into a collection basin surrounding the spinning disk and containing a gelling solution. Upon contact with the gelling solution, the polymer gels and provides a coating for the encapsulated biological tissue.

This invention thus typically comprises at least (1) a bead forming cup mounted for rotation about its central axis which is capable of projecting the formed beads outward, (2) a biological tissue and polymer containing suspension supply system containing the tissue to be encapsulated suspended in a coating polymer solution, and accurately metering particles and coating polymer solutions inside the bead forming cup, (3) means to determine and set the distance between dispensing needles and surface of droplet forming cup which can optionally be a conductivity data acquisition program/digital gauging probe, and (4) a collecting basin surrounding the bead forming cup axially concentric around the spinning bead forming cup containing a gelling solution. The collecting basin is mounted for rotation about its central axis and positioned to collect beads projected outward from the bead forming cup. The bead forming cup is connected to a rotational motor drive with an adjustable speed. The collecting basin is also connected to an independent rotational motor drive with an adjustable speed.

The spinning bead forming cup may or may not have a mixing chamber in the bottom. The walls of the spinning cup mixing chamber form an angle of 3–10 degrees with the central axis. The mixing chamber has an upper boundary from which a contiguous bead forming surface extends outward. If the cup does not have a mixing chamber, the bottom and the bead forming surface are contiguous. The bead forming surface is at an angle with the central axis which is sufficient to establish surface contact with the droplets. The bead forming surface angle with the central axis can be from 0 up to less than 90, preferably from 10 to 85 degrees with the central axis of the mixing chamber in a plane through the central axis thereof.

The surface of the bead forming surface of the spinning droplet forming cup can be smooth or textured and can have a coating which interacts with the beads to increase the surface-bead interaction. For example, the surface can be roughened with fine abrasive, such as fine sand paper or steel wool, wiped across the surface in a radial direction, or the surface can have radial grooves. This surface roughening will reduce the depth of coating on the particle.

The bead forming cup has an adjusting alignment which is used to center the cup and direct the beads into the gelation solution in the collecting basin. This adjusting alignment can be advantageously incorporated into the conductivity data acquisition program/digital gauging probe system which is optionally used to set the distance between dispensing needles and bead forming cup.

The suspension supply system is composed of one or plurality of containers, such as a syringe or syringe pump connected to a needle, for storing the suspension of particles, such as islets, to be encapsulated with a primary calcium/alginate coating and accurately metering and dispensing particles and multiple coating polymers. The particles to be encapsulated and the multiple coating polymers can be dispensed individually or simultaneous via separate multiple containers connected to separate regular or concentric needles. Utilization of the off-center positioned regular or concentric needles allows both a mass production of almost uniformly sized small droplets without substantial production of blank spheres, as well as the coating of a particle with multiple layers of the same or different polymers. The concentric needles also allow the generation of a calcium/alginate gradient halo layer between the different layers of polymer as described in the U.S. Pat. No. 5,578,314, incorporated by reference.

The particles and polymers can be dispensed on any portion or multiple portions of the bead forming surface. If the particles and polymer are dispensed utilizing two or more concentrically positioned needles they may be dispensed in two or more locations on the droplet forming surface. In the most preferred embodiment, the needle or needles are positioned so closely to the bead forming surface that the suspension flows and is not dropped from the needle(s) in a continuous stream.

In order to position the dispensing needles vis-a-vis the spinning disk surface correctly, their position is manually adjusted and the sizes of beads formed by spinning at that position are checked under microscope, or a location device such as a conductivity data acquisition program/digital gauging probe, commercially available, is utilized to determine the distance between the dispensing needle and the bead forming surface. In this instance, the device zeros when the needle is in contact with the bead forming surface. The bead forming surface is preferably in lower range from about $100\mu$ to about $300\mu$ to give the desired coating thickness.

The collection basin is typically comprised of the first annular channel (gelation channel) having upper and lower rims extending inward toward its central axis. The lower rim defines a second annular channel (collection channel). This second channel has downwardly converging inner and outer surfaces and is convergent with a U-shaped annular collection trough. The inner surface of the trough extends upward and is contiguous with the collection channel wall. The collection basin can comprise a plurality of adjacent annual channels, each channel having upper and lower rims extending inward toward its central axis, each lower rim thereof defining a second annual collection channel. Preferably, the diameter of adjacent channels are not the same.

All possible variations of the spinning disk apparatuses, as long as the needles of the suspension supply system are off-center or concentrically positioned are intended to be within the scope of the invention.

The process for coating particles is comprised of introducing, using a syringe pump, a suspension of the particles comprising biological tissue suspended in a solution of coating polymer, to the cup spinning about its central axis. The suspension is introduced either by dropping or preferably by a continuous flow directly onto the surface of the wall of the spinning cup. The operating speed of the spinning cup is typically between 1,000 to 30,000 rpm. The cup has an upwardly diverging bead forming surface and an outer edge.

The particles or tissue, surrounded by coating material for beads which, by centrifugal force of the spinning disk, travel up the bead forming surface. The coating becomes thinner and thinner further it travels, but it remains of the uniform thickness as the particles spin up the surface. The speed of the suspension supply syringe pumps, the rotating speed of the cup and the distance of the needle(s) from the bead forming surface determine the coating thickness, shape, and size of the final bead.

The location and distance between the dispensing needle and the bead forming surface also determines the coating thickness, shape and size of the final bead. The number, single or multiple, and configuration of the concentric dispensing needles, that is their position vis-a-vis the surface of the spinning disk affects the coating thickness, shape, and size of the final droplet. The closer to the wall the needle is, the smaller the formed droplets are. The composition and viscosity of the coating polymers dispensed via the single multiple or concentric needles also affects the coating thickness, shape, and size of the final bead. The concentration of various cations that are dispensed with the particles and coating polymers via the multiple or concentric needles affects the thickness and shape of the calcium/alginate gradient between the polymer layers.

The spinning cup and collection basin are rotating in the same direction and the speed of the collection basin is selected to minimize the impact speed of the beads. When the coated bead reaches the outer edge of the cup, the coated particles is projected outward from its central axis and drops into a gelation media in the spinning collection basin. The coating polymer and gelation media are selected to react to form a solid bead comprised of the gelled alginate in a divalent cation, preferably calcium, barium or strontium chloride. The coating material is gelled, fixed or polymerized in the collecting basin solution.

After the particles are coated, the bead forming cup and collecting basin rotation is stopped and the coated particles and gelation solution slide down from the gelation channel to the collection channel or container. The coated particles are recovered from the collection trough or container.

In the preferred embodiment, the spin disk encapsulation apparatus also includes a particle suspension supply system for storing the particles to be encapsulated in a coating polymer solution, and accurately metering and introducing particles and coating polymer suspension directly on the wall of the droplet forming spinning cup. To determine and set the distance between the dispensing needles and the droplet forming inner surface of the spinning cup, the sizes of the formed droplets are checked under microscope or some system, such as conductivity date acquisition program/digital gauging probes, is utilized.

The spinning cup is adjustably rotatable about its central axis, and the collection basins are independently rotatable and positioned to collect droplets projected from the spinning cup. The spinning cup includes a mixing chamber for receiving a supply mixture of a suspension of particles to be encapsulated and an appropriate coating solution. The mixing chamber extends into a generally diverging conically shaped sidewall, such that coating of the particles becomes thinner as the coated particles travel along the sidewall. The conically shaped sidewall includes an inner surface which can be smooth or textured for altering and controlling the thickness of the coating.

The coating apparatus further includes an elevation adjustment system for adjusting the alignment of the spinning cup with respect to the collection basins in the axial direction. The rotational speeds of the cup and the collection basins are selected so as to minimize the impact of the droplets against a capture solution in the gelation chambers of the collection basins.

Figure 7:
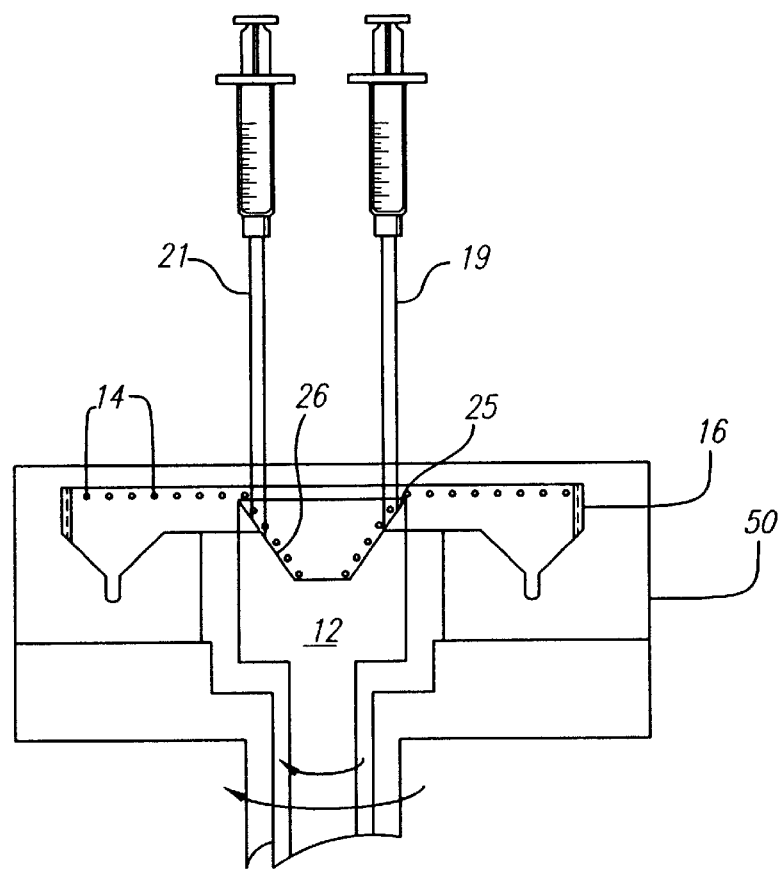
FIG. 7 is a cross-sectional view of the improved spin disk encapsulation apparatus showing the use of two off-center positioned needles to supply the particle and polymer mixture to the inner surface of the spinning cup of the spin disk encapsulation apparatus.
Figure 8:
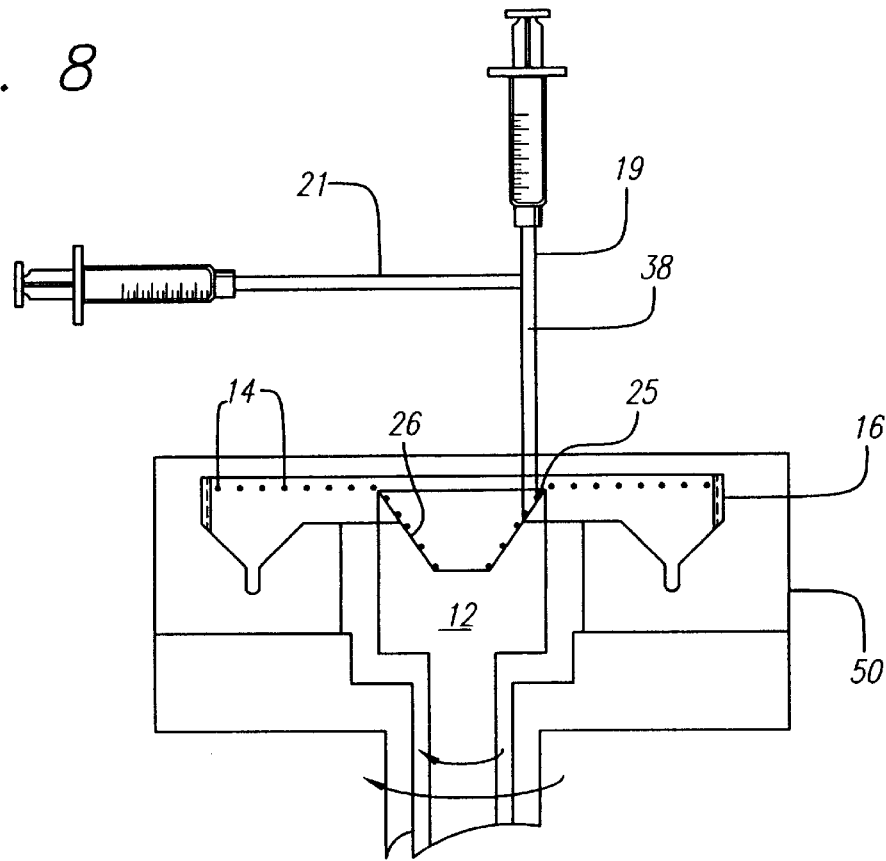
FIG. 8 is a cross-sectional view of the improved spin disk encapsulation apparatus showing the use of two concentric needles positioned off-center to supply the suspension of the tissue particles and polymer through one needle or separately through two needles to the inner surface of the spin disk encapsulation apparatus.
Figure 9:
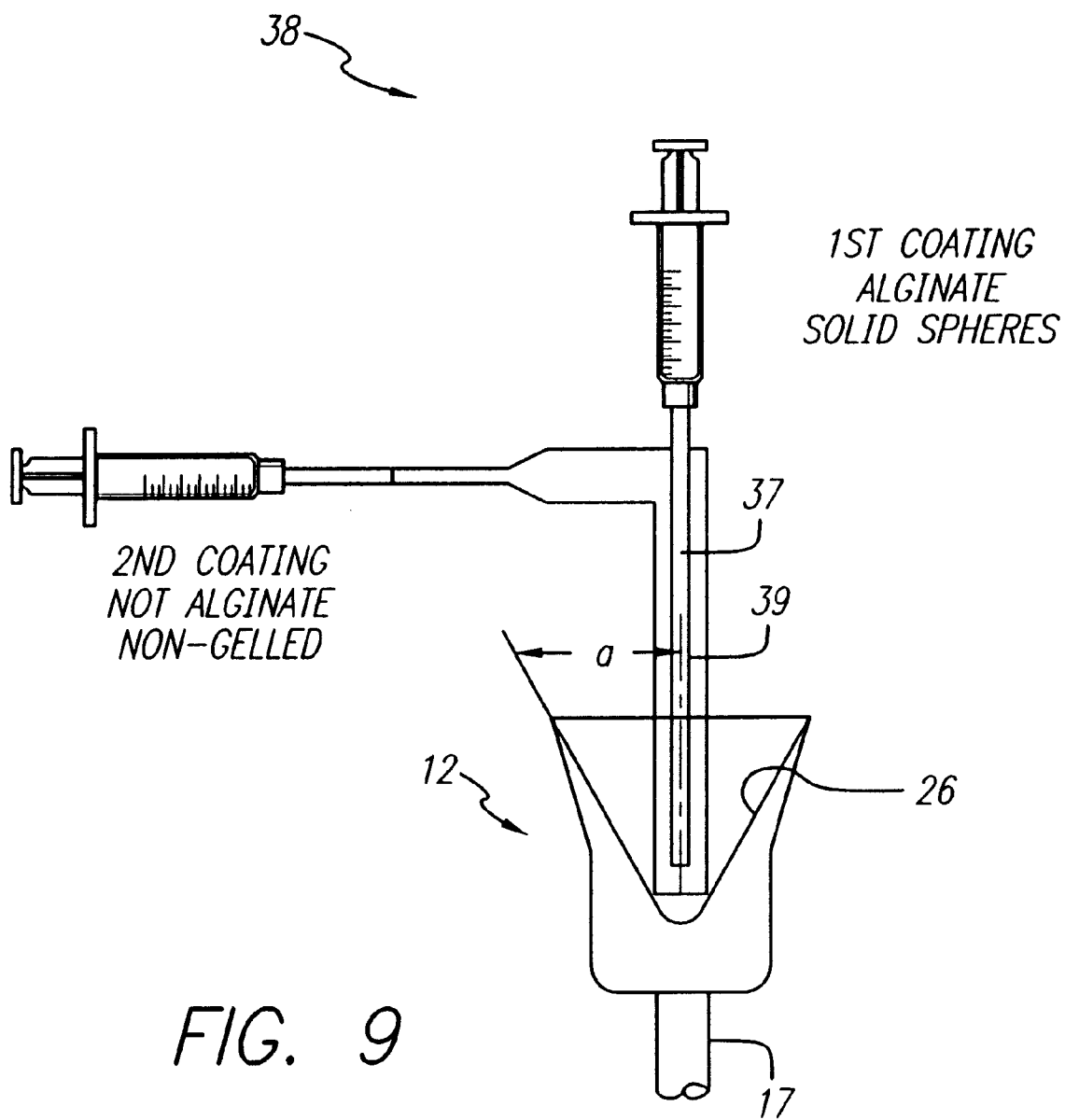
FIG. 9 is an enlarged cross-sectional view of the particle/polymer mixture supply system positioned centrally showing two concentrical needles of the improved spinning cup of the spin disk encapsulation apparatus.

In use for a method of preparing uniformly coated tissue, a supply mixture is introduced into the mixing chamber of the spinning cup from a suspension supply system composed of one or more off-center positioned needles, where the particles to be encapsulated are stored, and from which needles the particles and multiple coating polymers are dispensed. The particles to be encapsulated and the multiple coating polymers can be dispensed individually or simultaneously via separate multiple needles as shown in FIG. 7, or preferably concentric needles as shown in FIGS. 8 and 9 which are positioned centrally or off-center. Utilization of concentric needles and positioning the needles off-center allows the coating of a particle with multiple layers of the same or different polymers. The use of concentric needles seen in FIG. 9 also allow the generation of a calcium/alginate gradient halo between the different layers of polymer.

A suspension of tissue and polymers can be dispensed via needles on any portion or multiple portions of the droplet forming inner surface of the spinning cup. If the particles and polymers are dispensed utilizing two or more needles they may be dispensed in two or more locations on the droplet forming inner surface of the spinning cup. To achieve the desired thickness of the polymer coating of the particle to be encapsulated the spin disk encapsulation apparatus utilizes a system, such as for example, a conductivity data acquisition program or digital gauging probe, to determine and set the exact distance between the dispensing needle and the inner surface of the spinning cup where the droplets are formed which assures formation of the beads having the same size. Such device zeros when the dispensing needle is in contact with the inner surface of the spinning cup.

The droplet forming surface is positioned preferably from about $100\mu$ to about $300\mu$ from the dispensing needles to give the desired coating thickness of $20$–$200\mu$, preferably thickness from about $20\mu$ to about $150\mu$. As the spinning cup spins, the coated particles are propelled upward by the centrifugal force from the mixing chamber along the inner surface of the spinning cup, and are projected radially outward, as beads, into a gelling or capture solution of divalent cations, such as calcium, in one of the selected collection basins. Since the spinning cup and the collection basin are simultaneously rotating, the impact of the droplets against the capture solution in the selected collection basin is significantly minimized.

The spin disk encapsulation apparatus and method according to the present invention are highly effective for applying continuous, uniform smooth coatings having thickness from about 20 to about $200\mu$ on transplantation tissues, cells or cell lines, with a high degree of control and reproducibility and at coating rates to provide quantity of coated tissue microcapsules. The produced microcapsules have the effective volumes and diameters required for transplantation by injection through standard needle gauges. The apparatus and method are also useful for forming small, uniform droplets containing tissues, cells or cell lines suitable for biochemical manufacture of products of the tissues, cells or cell lines in suitable media.

Any type of tissues, cells or cell lines for which transplantation is desired can be coated and transplanted according to this invention. The most important tissues for transplants are secretory organ tissues, where transplantation from a donor organ to a host animal is desired to at least partially replicate the donor organ's action in the host system. Preferred donor tissues are pancreatic islets, hepatic cells, neural cells, renal cortex cells, vascular endothelial cells, thyroid cells, adrenal cells, thymic cells and ovarian cells. It has been experimentally found that for secretory tissues such as pancreatic islets, the thickness of protective porous coatings in the range of from 20 to $150\mu$ is most preferred. The coatings must also have the permeability required to permit effective diffusion of the encapsulated nutrients and other essential biological materials to the transplanted tissues and passage of transplant tissue products therefrom into the host system. The coatings preferably exclude immunologically effective concentrations of agents of the host immune system from the transplant tissue.

The improved spin disk apparatus of the present invention, therefore, produces transplant tissue coatings having these essential characteristics with high efficiency and product volumes required to replace or supplement an organ function in a human host.

DETAILED DESCRIPTION OF THE DRAWINGS

The above and other features of the present invention and the manner of attaining them, will become apparent, and the invention itself will be best understood, by reference to the following description and the accompanying drawings.

Figure 2:
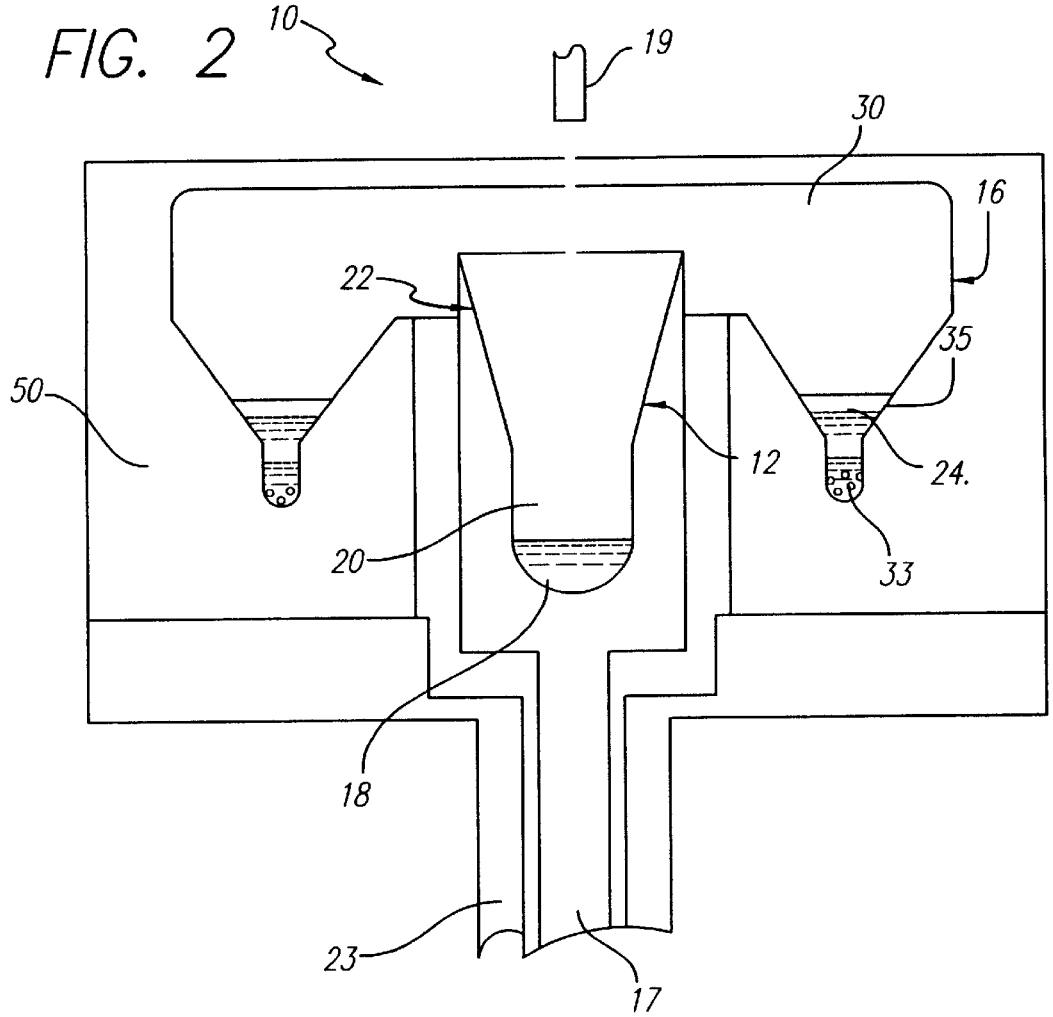
FIG. 2 is another schematic side elevational view of the spin disk encapsulation apparatus of FIG. 1, after the encapsulation process is completed.

Referring now to the drawings, FIGS. 1 and 2 illustrate two schematic side elevational views of a spin disk encapsulation apparatus 10 which is provided to perform the encapsulation process according to the present invention. The spin disk encapsulation apparatus 10 generally includes a spinning cup 12 (or disk), for forming droplets 14 (or beads) and for projecting them centrifugally into a rotatable collection basin 16, which substantially surrounds the spinning cup 12.

Figure 5:
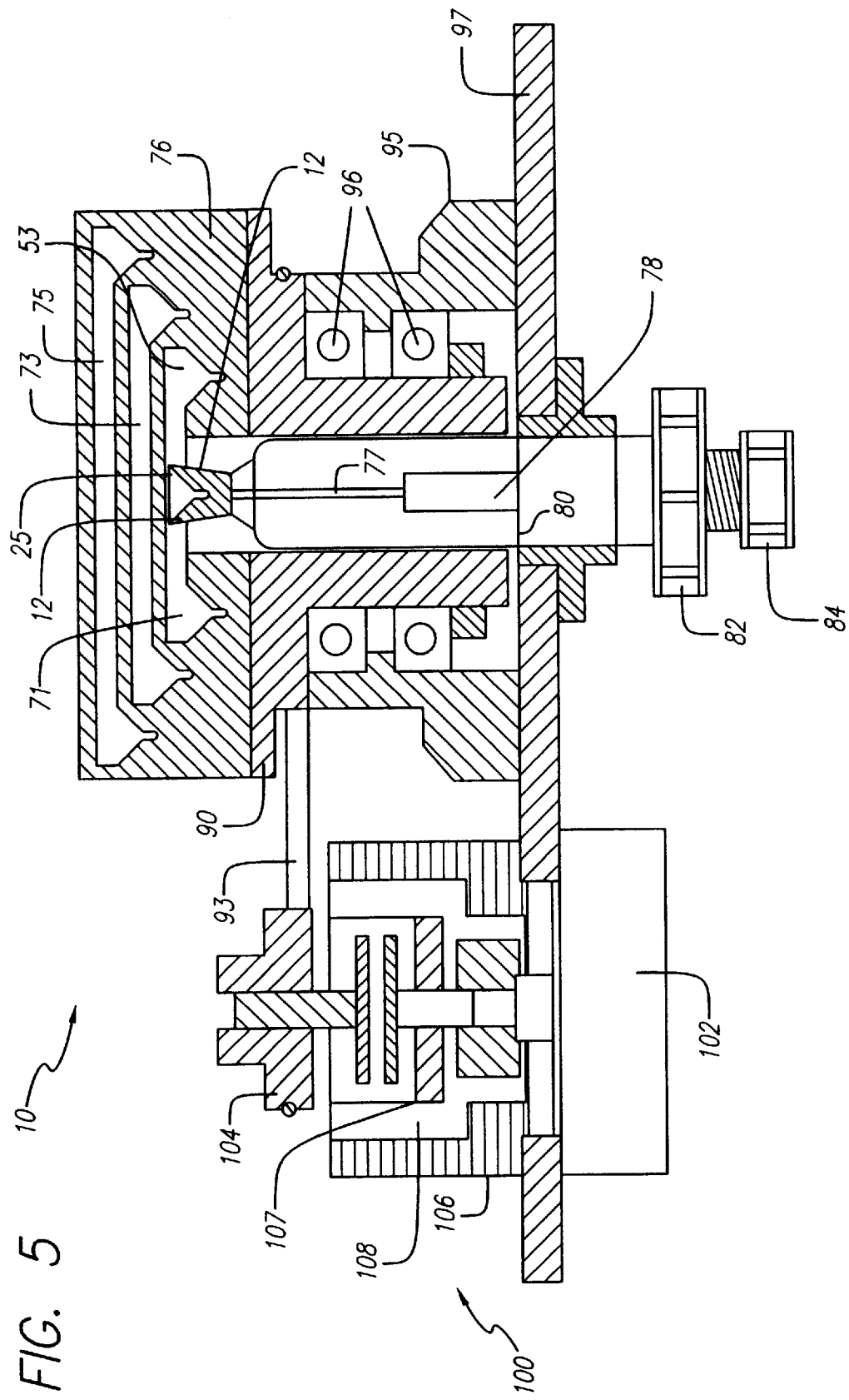
FIG. 5 is a cross-sectional view of the preferred embodiment of the spin disk encapsulating apparatus according to the present invention, which uses the encapsulation method of the apparatus of FIGS. 1 and 2.

The spinning cup 12 is connected to a source of rotary power, such as a motor seen, for example, in FIG. 5, via a spinning cup drive shaft 17 (or rotor), for rotation about its central axis. The spinning cup 12 receives a supply mixture 18 of a suspension of particles, such as islet tissues, cells or cell lines, in a solution of a coating polymer, such as alginate, agarose, etc., via a syringe needle 19 (or some other conduit or tube). The spinning cup 12 may or may not include a mixing chamber 20, which extends into an upwardly diverging, conical sidewall 22, and which terminates into an upper rim 25. If the spinning cup does not have a mixing chamber, the bottom of the cup and the droplet forming inner surfaces are contiguous. The spinning cup 12 is designed to project the droplets 14 radially outward along a generally horizontal trajectory. The rotational speed of the spinning cup 12 is adjustable.

The gelation chamber or channel 30 is defined within the block 50, and extends into the collection chamber or channel 35. The gelation chamber 30 is annular, and is defined by an upper rim or edge 52 which is substantially flat, and which extends generally horizontally and radially from the central axis into a vertical or lateral sidewall 53, which, in turn, extends into a first conical or beveled edge 55 of the collection chamber 35.

The collection basin 16 coaxially surrounds the spinning cup 12, for collecting the droplets 14 projected by the spinning cup 12. The collection basin 16 is connected to a source of rotary power, such as a motor, via a collection basin drive shaft 23 (or rotor), for rotating about its central axis. The rotational speed of the collection basin 16 is also adjustable. The spinning cup 12 and the collection basin 16 are independently connected to different motors, such that their rotatable speeds are separately adjustable in order to minimize the impact of the droplets 14 against a gelling solution 24 in the collection basin 16.

In use, the supply mixture 18 is introduced into the spinning cup 12, via the needle 19. An adjusting alignment has been incorporated into a conductivity data acquisition program or digital gauging probe which is used to set the distance between dispensing needles 19, 37, 39 and the inner surface 26 of the spinning cup 12. The rotational speed of the spinning cup 12 is selected to best suit the coating application. In the preferred embodiment, the rotational speed ranges between 1,000 rpm (revolutions per minute) and 30,000 rpm. The variability of the rotational speeds of the spinning cup 12 and the collection basin 16 of the spin disk encapsulation apparatus is intended to be within the scope of the invention.

As the spinning cup 12 spins, the suspension surrounded by the coating is propelled by the centrifugal force from the mixing chamber 20, and travels along the inner droplet forming surface 26 of the beveled sidewall 22. The coating becomes thinner as the coated particles travel along the inner droplet forming surface 26. It has been experimentally determined that the rotational speed of the spinning cup 12, the travel distance of the coated particles along the inner droplet forming surface 26, and the texture of the inner droplet forming surface 26 determine the coating thickness, shape, and size of the final droplets 14. The coating thickness decreases with the coarseness of the inner droplet forming surface 26 and increased spinning speed of the spinning cup 12 and the thickness of the coating thus may be advantageously manipulated by changing the texture of the inner droplet forming surface 26 and the speed of the spinning cup 12.

The rotational speed of the basin block 50 is sufficient to cause the gelling solution 24 to travel upward from the collection chamber 35 and to accumulate in the lateral gelation chamber 30. As the basin block 50 rotates, the gelling solution 24, which is initially at rest in the collection trough 59, is propelled by the centrifugal force along the surface of the first beveled edge 55 and accumulates against the vertical sidewall 53, within the lateral gelation chamber 30. When the encapsulation process is completed, and the collection basin 16 stops, the microcapsules 33 gelled by the gelling solution 24 fall back down, along the surface of the first beveled edge 55, into the collection trough 59, where the microcapsules 33 are retrieved.

When the coated particles reach the upper rim 25 of the spinning cup 12, they are projected radially outward, as spherical droplets 14 into the gelling solution 24. The coating polymer, preferably an alginate and the gelling solution 24, preferably calcium chloride, are selected to interact upon contact where the alginate is gelled by the calcium chloride and forms solid droplets or microcapsules 33. Since the collection basin 16 is also spinning, the gelling solution 24 is propelled by the centrifugal force, into a lateral gelation chamber 30 which is positioned to capture the droplets 14 propelled from the spinning cup 12. The coating material is gelled, fixed or polymerized in the lateral gelation chamber 30.

The spinning cup 12 and the collection basin 16 are generally rotated in the same direction, and their rotational speeds are selected to minimize the impact of the droplets 14 against the gelling solution 24, since the impact of the droplets 14 against the gelling solution 24 can deform or damage the droplets 14. By simultaneously rotating the spinning cup 12 and the collection basin 16 in the same direction, the impact of the droplets 14 against the gelling solution 24 is significantly reduced.

As illustrated in FIG. 2, after the encapsulation process is completed, the flow of the supply mixture 18 is interrupted, and the spinning cup 12 and the collection basin 16 are stopped. The supply mixture 18 is collected inside the mixing chamber 20 of the spinning cup 12, and the microcapsules 33 and the gelling solution 24 slide down from the lateral gelation chamber 30 to a collection chamber 35 of the collection basin 16. The microcapsules 33 are then recovered from the collection chamber 35. Fresh gelling solution 24 can be introduced into the collection chamber 35, while the spin disk encapsulation apparatus 10 is stationary or after it starts rotating.

As mentioned previously, the thickness of the droplet coatings can be adjusted by changing the rotational speed of the spinning cup 12, the texture of the inner droplet forming surface 26 and the travel distance of the coated particles along the inner droplet forming surface 26. The overall shape of the droplets 14 can also be adjusted by the changing the distance between the spinning cup 12 and the lateral gelation chamber 30 of the collection basin 16. Additionally, the thickness and the overall diameter of the droplets 14 can be adjusted by texturing the inner droplet forming surface 26 of the beveled sidewall 22 of the spinning cup 12, and adjusting the travel distance of the coated particles along that inner droplet forming surface 26. As the coated particles travel upward along the inner droplet forming surface 26, the thickness of the coating interacts with the inner droplet forming surface 26, and is gradually reduced.

The collected microcapsules 33 can be recycled (e.g., by repeating the foregoing encapsulation process), in a fresh supply mixture 18 for applying one or more additional coatings on the microcapsules 33, in order to ensure that the biological particles are completely coated and encapsulated.

The preferred coating solutions are sodium alginate solutions of non-fibrogenic alginates, as described in U.S. Pat.

No. 5,429,821. Other suitable coating polymers include any polymers which have the desired characteristics. The coating solutions are selected to quickly solidify or polymerize upon contact with the gelling solution 24. For example, suitable alginates polymerize upon contact with an aqueous solution containing polyvalent metal cations such as calcium and strontium ions. The gelling solution 24 is constituted to provide the component required to polymerize or solidify the polymer coating. Polysaccharides such as agarose which solidify upon contact with chilled liquid can also be used. Droplets comprising suspensions in a polyvalent metal ion solution in water can be captured in a sodium alginate solution to form an encapsulated suspension. It will be readily apparent to a person skilled in the art that a wide variety of tissue to be coated, polymers, and gelling solutions, can be used in the apparatus and method of this invention, and it is intended to include all suitable tissues, polymers, or gelling solutions, in the use of the apparatus of this invention.

Figure 3:
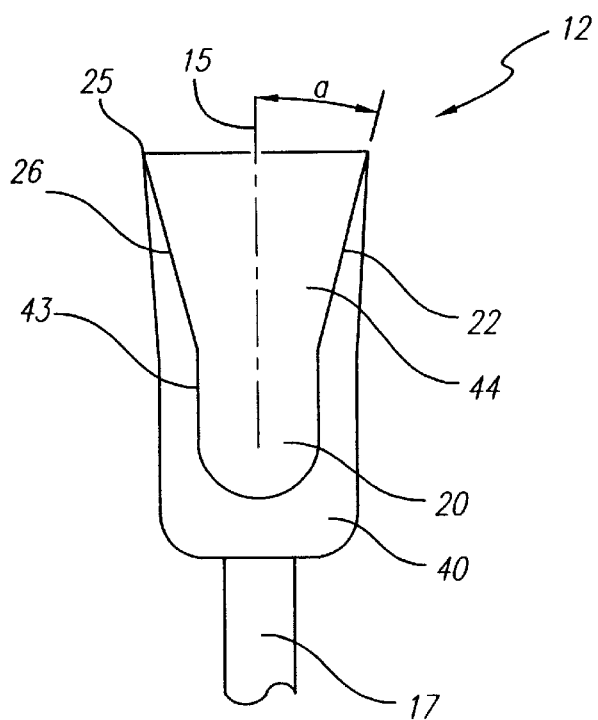
FIG. 3 is an enlarged schematic view of a spinning cup used in the spin disk encapsulation apparatus of FIGS. 1 and 2.

Considering now the spin disk encapsulation apparatus 10 in greater detail, FIG. 3 is an enlarged schematic view of the spinning cup 12. The spinning cup 12 includes a block 40 which is connected to the spinning cup drive shaft 17 for rotating therewith. The mixing chamber 20 is defined within the block 40, for retaining the supply mixture 18. The mixing chamber 20 is hollow throughout its axial length, and is open at its upper end. In the preferred embodiment, the mixing chamber 20 includes a substantially cylindrical sidewall 43, which forms a diverging angle of less than 5 degrees with the central axis of rotation of the spinning cup 12, which is illustrated by a broken line. It should however be understood that another inclination or angular deviation are also contemplated by the present invention. This angular deviation will allow the supply mixture 18 in the mixing chamber 20 to progressively travel along the cylindrical sidewall 43, toward the beveled sidewall 22. The spinning cup 12 can be a flat disc, V-shaped, or it can have any other appropriate shape.

Also defined within the block 40 is an upper chamber 44, which is bound by the beveled sidewall 22, and which terminates, at the upper end of the block 40, in the upper rim 25. The upper rim 25 can be sharp and thin, or shaped to change the characteristics of the projected droplets 14. The beveled sidewall 22 forms an angle "a" with the central axis of the mixing chamber 20. The angle "a" is generally less than 90 degrees, and preferably ranges between 10 degrees and 85 degrees. The angle "a" is selected such that the beveled sidewall 22 establishes a sufficient contact surface area with the coated particles, during their upward travel to the upper rim 25.

The inner droplet forming surface 26 of the beveled sidewall 22 can be smooth or roughened. Preferably, the inner droplet forming surface 26 is roughened or textured by means of outwardly extending shallow grooves or lines (not shown), when the angle "a" is greater than a predetermined value, such as 70 degrees. These grooves or lines can be formed with any sharpened instrument designed for this purpose or with an abrasive material such as fine sand paper or steel wool, by moving the instrument or abrasive material across the inner droplet forming surface 26 in the radial direction. This texturing will reduce the thickness of the coating on the particle. The spinning cup 12 is adjustable along the vertical or axial direction, such that the droplets projected from the spinning cup 12 are directed into the gelling solution 24 in the collection basin 16. The rotational speed of the spinning cup 12 is determined by the desired thickness of the coatings.

Figure 4:
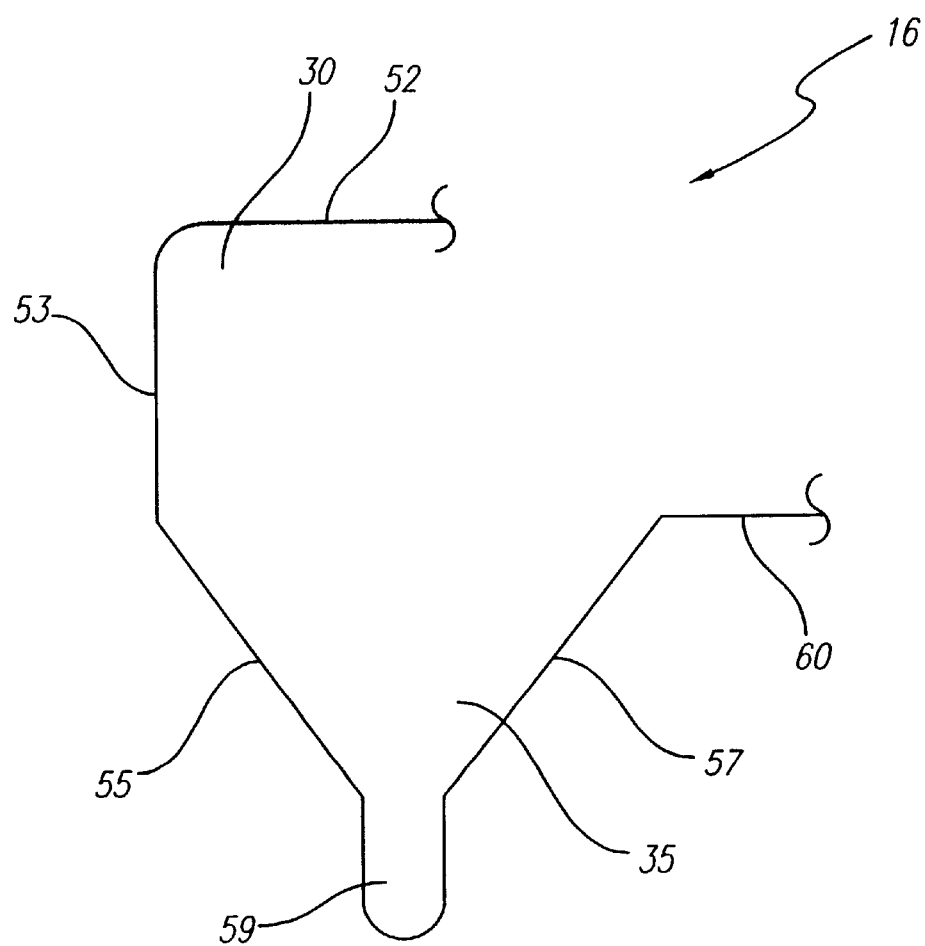
FIG. 4 is an enlarged partial schematic view of a collecting basin used in the spin disk encapsulation apparatus of FIGS. 1 and 2.

FIG. 4 illustrates a partial schematic representation of the collection basin 16. The collection basin 16 generally includes a block 50, as illustrated in FIGS. 1 and 2, which is connected to the rotor or shaft 23, for connection to a motor. The shaft 23 is preferably hollow throughout at least some of its axial length, for surrounding the shaft 17, such that both shafts 17 and 23 are independently rotatable at selected speeds.

The collection chamber 35 is also annular, and is defined by the first beveled edge 55, and a second beveled edge 57, which converge into a generally U-shaped annular collection trough 59. The second beveled edge 57 is generally symmetrical to the first beveled edge 55 with respect to a central geometric axis of the trough 59. The second beveled edge 57 extends radially into a substantially flat lower rim or edge 60 parallel to the upper rim 52. The rim 60 extends inwardly toward the block 40 of the cup 12.

The spin disk encapsulation apparatus 10 provides a sterile environment for the encapsulation process. In one embodiment, the collection basin 16 is completely enclosed, and filled with sterilized air, at room temperature and at atmospheric pressure. It should become clear that the collection basin 16 can alternatively be filled with another fluid medium or ionized particles, at various temperatures and pressures to generate the desired microcapsules.

The spin disk encapsulation apparatus 10 of the present invention is particularly suitable for encapsulating or coating biological tissues, because even fragile tissues such as pancreatic islets or beta cells are not significantly destroyed or damaged when their suspension in alginate is shaped into droplets by the spinning and the droplets are gelled by contact with the gelling solution. The coatings generated by the present spin disk encapsulation apparatus is therefore sufficiently thin, continuous and non-fibrinogenic and therefore, the rejection of transplanted coated and xenograft tissues is prevented. By using the present spin disk encapsulation apparatus 10, it is possible to generate protective coatings having a thickness in the range of $20\mu$ to $200\mu$, preferably about $150\mu$ which allows transport of nutrients, cell waste products and hormones.

The rotational speeds of the spinning cup 12 and the collection basin 16 are selected so as to minimize the impact of the droplets 14 as they are propelled into the gelling solution 24. In this respect, as the droplets 14 leave the spinning cup 12, they are not propelled in a strict radial way, but are rather gyrated such that the vectorial representation of their rotational speed has a radial component Vr which is generally normal to the contact surface of the gelling solution 24, and a tangential component Vt, which is perpendicular to the radial component Vr. In one embodiment according to the present invention, the rotational speed Vb of collection basin 16 is rendered equal to the tangential component Vt. Since the collection basin 16 is rotating in the same direction as the spinning cup 12, the speed of the collection basin 16 relative to the tangential component Vt of the rotational speed of the spinning cup 12 is about zero, and as a result, only the radial component Vr will affect the impact of the droplets 14 against the gelling solution 24. It is also possible to minimize the radial component Vr and thus the bead impact against the gelling solution 24, by further balancing and controlling the rotational speeds of the spinning cup 12 and the collection basin 16.

FIG. 5 is a cross-sectional view of a complete set-up of one of the preferred embodiments of a centrifugal spin disk encapsulating apparatus 10 according to the present invention. The spin disk encapsulation apparatus 10 generally includes the spinning cup 12 (or disk) for forming droplets 14 (or beads) and for projecting them centrifugally into a selected one of a plurality of rotatable collection basins 71, 73 and 75 which substantially surround the spinning cup 12.

The collection basins 71, 73 and 75 are formed within a single block 76. While three collection basins are shown, it should become clear that a different number of basins may alternatively be selected. The operation of the spin disk encapsulation apparatus 10 further includes the ability to select one of a plurality of collection basins 71, 73 or 75, by adjusting and aligning the spinning cup 12 with the selected basin. The diameters of the collection chambers of the collection basins 71, 73 and 75 are different, preferably increasing from bottom to top. In the preferred mode, the diameters of the collection chambers can vary between 3 inches and 2 feet.

The spinning cup 12 is mounted on spinning cup drive shaft 17, which is connected to a high speed motor 78, which can optionally be a variable speed motor. The operating speed of the high speed motor 78 is preferably in the range from 1000 to 30,000 rpm. The high speed motor 78 is mounted on a platform 80 connected to a conventional threaded coarse vertical adjustment wheel 82 and to a fine adjustment knob 84.

The rotation of the vertical adjustment wheel 82 about its central axis raises or lowers the platform 80 in the vertical direction, thus axially raising or lowering the spinning cup 12, for roughly aligning its rim 25 with a selected one of the collection basins 71, 73 or 75. The rotation of the fine adjustment knob 84 about its central axis raises or lowers the platform 80 in the axial direction, for precisely aligning the upper rim 25 of the spinning cup 12 with the gelling chamber of the selected collection basin. FIG. 5 shows the upper rim 25 aligned with the collection basin 71. Preferably, the upper rim 25 is aligned with the center of the vertical sidewall 53 of the collection chamber of the selected basin, i.e., 71.

These vertical alignments can be carried out while both the spinning cup 12 and the block 76 are rotating, and the droplets 14 are being projected from the spinning cup 12 toward the collection basin, i.e., 71 in the present illustration. This will enable the adjustment of the elevation of the upper rim 25, and thus the impact level of the droplets 14. In the preferred embodiment, the optimal impact level is the center of the collecting liquid surface. Additionally, with these adjustments, it is now possible to produce coatings with a high degree of control and reproducibility, at a rapid rate, thus enabling the mass production of microcapsules 33.

The lower collection basin 71 includes a collection chamber with the smallest diameter. The adjustment of the upper rim 25 can be monitored visually or by means of appropriate video equipment. It should be readily apparent to a person skilled in the art that only one or any number of the collection basins 71, 73, 75 can be used, and the shape of the vertical sidewalls of their respective collection chambers can be varied and still obtain the functional equivalent properties of the spin disk encapsulating apparatus 10.

In one embodiment, the collection basins 71, 73, 75 are insulated from each other, such that each basin can be used as an independent basin, similar to the collection basin 16 described above. Thus, for illustration purpose, while the collection basin 71 is filled with a first fluid medium, at predetermined temperature and pressure, any one or more of the other collection basins 73 and/or 75 can be filled with another fluid medium, at a different temperature. One application for this embodiment is the multi-layer coating of the particles, where a first smaller coating is deposited using one of the collection basins, e.g., collection basin 75, then a second coating is deposited using the collection basin 73 and the third coating is deposited using the collection basin 71. It should be understood that the composition of the first, second and third coatings can be similar or different.

The block 76 is mounted on a generally cylindrically shaped rotary platform 90 having a grooved rim in which a drive belt 93 is received, for imparting a rotational motion to the platform 90, and thus to the block 76 and the collection basins 71, 73 and 75 defined therein. The rotary platform 90 is supported on an outer casing 95 by means of a plurality of bearings 96. A generally flat base plate 97 supports the outer casing 95 and a motor assembly 100 for rotating the collection basins 71, 73 and 75.

The rotational speed of the motor assembly 100 can be selected by any conventional variable speed system, for example, with a variable speed motor 102 or a clutch 106. In the present illustration, a drive pulley 104 is connected to the variable speed motor 102 via a clutch 106. The clutch 106 can be any conventional speed regulating system. The clutch 106 has a flexible coupling 107 and a clutch assembly 108.

Figure 6:
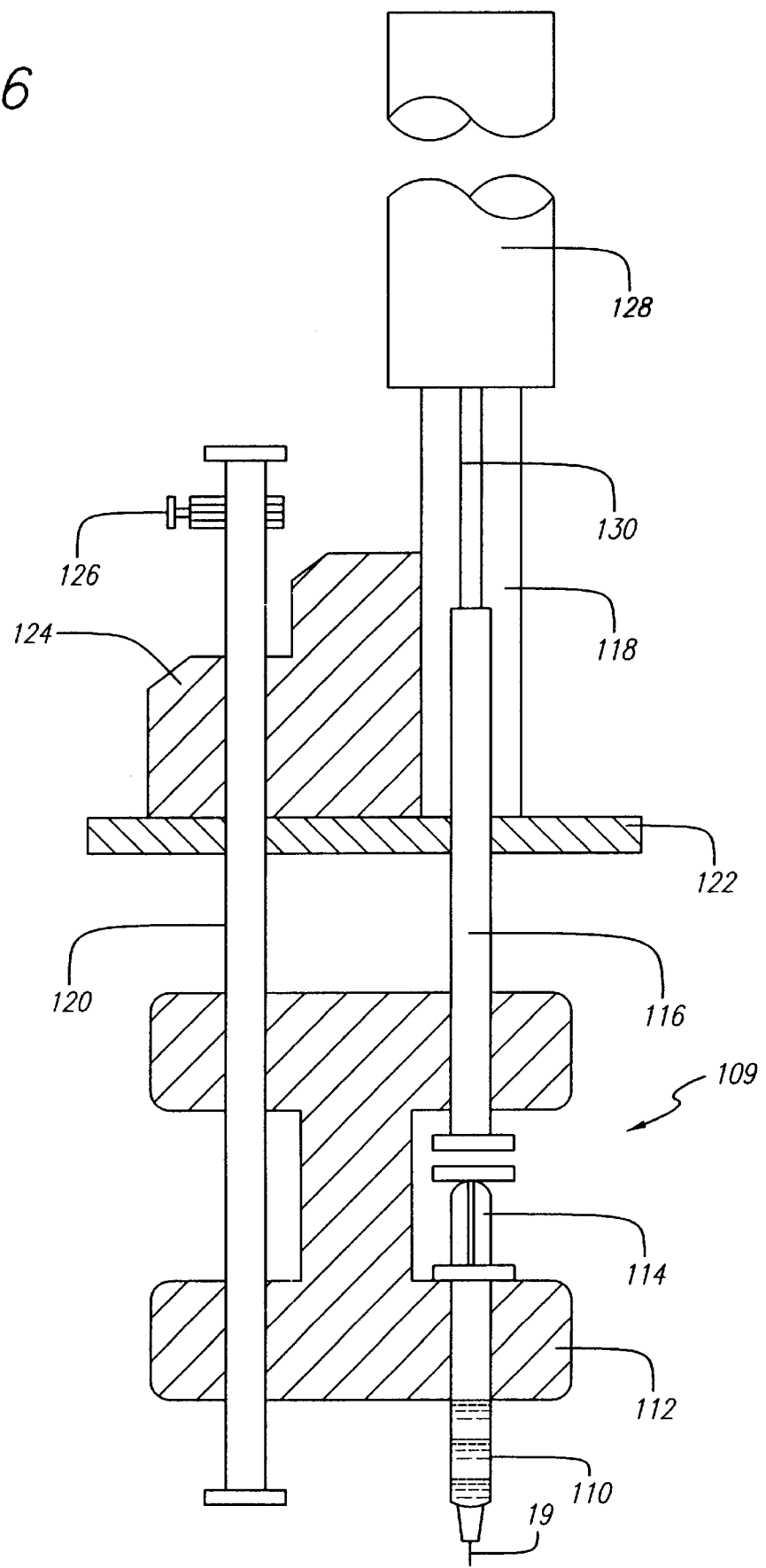
FIG. 6 is a schematic cross-sectional view of a suspension supply system according to the present invention, for use with the spin disk encapsulation apparatus of FIGS. 1, 2 and 5.

FIG. 6 is a cross-sectional view of one embodiment of a suspension supply system according to the present invention. The particles of islets to be encapsulated are suspended in an appropriate coating polymer solution, and are accurately metered by a syringe 109, or similar cylinder/plunger piston combination. The syringe 109 includes a barrel 110, which is supported by a clamp 112, and a plunger or piston 114 which is capable of moving telescopically within the barrel 110. A push rod 116 is mounted for vertical movement through part of the clamp 112 and through a cylindrical mount 118. The push rod 116 is positioned to depress the plunger 114 inside the barrel 110, when it is moved in the downward direction.

The clamp 112 is supported by a guide rod 120. It is secured to a mounting base 122, and extends through a reinforcement gusset 124. An adjustable stop 126 limits the downward position of the clamp 112. The gusset 124 is secured to the mounting base 122, and has a passageway through which the guide rod 120 extends. A hydraulic cylinder 128 is supported by the mount 118, and is connected to the push rod 116 by means of a rod connector 130. The downward displacement of the rod connector 130 by the hydraulic cylinder 128 causes a downward movement of the push rod 116 and thus the depression of the plunger 114, for discharging a precise flow of the suspension from the needle 19.

FIGS. 1–6 illustrate the spinning disk apparatus of the prior invention described in U.S. Pat. No. 5,643,594 where the needle supplying the suspension is positioned in the center of the spinning cup and the suspension is typically introduced as drops. While the above apparatus provides encapsulated particles having a reasonably high uniformity, it still produce a large number of empty spheres formed from the alginate alone without a presence of any tissue or cell transplant. This not only leads to a waste of the polymer and time in forming these empty spheres but also results in dilution of the final encapsulated transplant volume introduced into a transplant host and may also result in underestimating the actually administered number of coated transplants.

These disadvantages are overcome with the improvements introduced by the current invention.

The improvement of the current invention is illustrated in FIGS. 7–9.

FIG. 7 illustrates a partial schematic representation of the improved spin disk encapsulation apparatus 10. The general features of the spin disk apparatus are described in detail in FIGS. 1–6. In addition to the spin disk encapsulation apparatus described in FIGS. 1–6, the improved spin disk apparatus comprises off-center positioned regular needle or plurality of needles and/or concentrically placed plurality of needles. Optionally, the invention utilizes a conductivity meter, such as a devise combining a data acquisition program/digital gauging probe.

FIG. 7 further illustrates a multiple particle/polymer mixtures supply system. Needles 19 and 21, which are positioned off-center of the spinning cup, are either manually positioned and adjusted or are positioned according to the data provided by a conductivity data acquisition program/digital gauging probe system (not shown) which is commercially available, in such a way as to dispense the particles to be encapsulated at a certain predetermined distance above the droplet forming inner surface 26 of the spinning cup 12. The distance is predetermined, by manually checking the sizes of the formed beads or using the conductivity data acquisition program/digital gauging probe, to result in the desired size of the droplets 14 and the desired thickness of the polymer coating the droplets 14. Preferably, the needle or needles are positioned as close to the spinning disk wall surface as possible to achieve a stream of the suspension. If the suspension is dispensed utilizing two or more needles it may be dispensed in two or more locations on the droplet forming inner surface 26 of the spinning cup 12 and may result in formation of droplets having different sizes, which may be desirable for certain uses.

In the particular set-up seen in FIG. 7, beads formed from the suspension introduced by the needle 19 will be smaller and have a thinner coating than the beads formed from the suspension introduced by the needle 21. The needle 21 is positioned closer to the upper rim 25, the beads therefore travel a shorter distance before being propelled outward by spinning. These beads will have a larger overall size, thicker coating and there may be a certain number of blank spheres present. The beads formed from suspension introduced by needle 19 travel a longer distance and are therefore smaller, have a thinner coating and there are very few or no blank spheres.

FIG. 8 illustrates an embodiment of the improved spin disk encapsulation apparatus 10 shown in FIG. 1, designed to allow multiple polymer coating of the particle to be encapsulated prior to encapsulation.

FIG. 8 shows an off-center placed concentric needle suspension supply system 38, which allows the coating of a particle with multiple layers of the same or two or more different polymers. The two or more concentric needles, herein seen as needles 19 and 21, are positioned off-center manually or using a conductivity meter to dispense the suspension of the particles to be coated, needle 19 and one other polymer, needle 21, onto the bead forming inner surface 26 of the spinning cup 12. The particle dispensing needle 19 is shown to be surrounded by the polymer dispensing needle 21. Both the suspension of the particles in the first polymer from needle 19 and the second polymer alone from needle 21 are introduced onto the surface of the rotating spinning disk and the microcapsules containing the tissue particle in the middle, covered with the first polymer and then with the second polymer are generated and dropped into the gelling solution.

In one embodiment the needle 19 may introduce a suspension of the tissue in one particular polymer and the second needle 39 may introduce the second polymer having a different molecular weight so that the tissue is first coated with the first polymer and then with the second polymer surrounding the first polymer. In this fashion an additional third coating may be added, or, in still another embodiment multiple needles 39 may be used to allow generation of a calcium/alginate gradient halo between the different layers of the polymers. In such an event still another concentrically positioned needle (not shown) is used.

FIG. 9 is a close-up view of the center positioned concentric needle suspension supply system 38 and spinning cup 12 portion of the spin disk encapsulation apparatus. The particle dispensing needle 37 is positioned manually or by the conductivity meter to dispense particle beads of the desired size. The polymer dispensing needle 39 is positioned to dispense the second coating polymer which results in the desired thickness and changes the permeability properties of the coating of the polymer surrounding the particle to be encapsulated. The complete suspension system may be positioned relative to any portion of the droplet forming inner surface 26 of the spinning cup 12 depending on the desired size of the particle and thickness of the polymer coating.

The coating thickness, shape and size of the final droplet are determined by the speed of the needles and the spinning cup; the length of the bead forming inner surface of the spinning cup each bead travels; the distance between the dispensing needle and the bead forming inner surface of the spinning cup; the location of the dispensing needles on the bead forming inner surface of the spinning cup; the size and configuration of the dispensing needles; and the composition and viscosity of the coating polymers dispensed via the single, multiple or concentric needles. The thickness and shape of the calcium/alginate gradient "halo" between the polymer layers coating the particle is affected by the concentration of various cations that are dispensed with the particles and coating polymers via the multiple or concentric needles.

Therefore, the present invention achieves significant advantages not yet attained by the conventional encapsulation systems and methods. The present spin disk encapsulation apparatus 10 and method can successfully be used for coating biological materials such as tissues, cells and cell lines and other semi-solid particles with a thin, uniform, continuous, and semi-permeable bio-compatible coating. Use of the improved spin disk encapsulation apparatus 10 of this invention, makes it now possible to produce coatings with a high degree of control and reproducibility, at a rapid rate, and thus enables mass production of microcapsules. It has been demonstrated that the encapsulation process, using the present invention, can generate about 100,000 microcapsules in less than five minutes. This is an important feature as a human transplantation of coated pancreatic islets, for example, requires from 3,000,000 to about 6,000,000 or more coated islets initially and replacement of several hundred thousand coated islets monthly.

The operation of the spin disk encapsulation apparatus of this invention is further illustrated by the following examples.

EXAMPLE 1

Preparation of High Guluronate Alginate

This example illustrates the preparation of alginates having high content of guluronate used as a first coating.

Eighty grams of protein alginate commercially available from Protan Biopolymers, Trondheim, Norway, were dissolved in 89 L water by rolling on a roller mill. The solution was filtered through a 50μ mesh to remove particles, and then mixed on a roller mill with 320 g of bleached, activated charcoal with continued mixing for 30 minutes. The activated charcoal was then removed by centrifugation for 30 minutes. The resulting solution was sequentially filtered through filter paper, a 0.45μ filter, a 0.22μ filter and a 0.1μ filter. 163 g magnesium chloride were then added to the solution and dissolved by rolling on a roller mill. 210 ml of a 1.7% calcium chloride dihydrate solution were then added and mixed by rolling on a roller mill for 30 minutes. The resulting solution was centrifuged for 30 minutes to produce an alginate pellet. The alginate pellet was dissolved in 3.0 liters of 0.1M EDTA, pH 7.0 by rolling on a roller mill. The pH of the solution was adjusted to pH 7.0, as needed. 20 g sodium chloride were then added to this solution and dissolved.

Alginate was precipitated from the solution by the addition of 5 L of neat ethanol, followed by centrifugation for 30 minutes to obtain an alginate pellet. The alginate pellet was then suspended in ethanol and tweezed apart with tweezers to insure complete washing of the sample. Excess ethanol was then removed by squeezing and pressing the precipitate. The alginate precipitate was then dried in an oven, under vacuum, at 60° C.

These alginates were then used for coating pancreatic islets, employing the spinning disc encapsulation apparatus of the present invention.

EXAMPLE 2

Preparation of High Mannuronate Alginate

This example illustrates the preparation of alginates having high content of mannuronate.

50 g low viscosity sodium alginate (LV Alginate, KELCO Div. of Merck & Co.) isolated from *Macrocystis pyrifera* were dissolved in 5 liters of water and filtered through a 50 micron mesh to remove particulates. 18.6 g tetrasodium EDTA were added to the solution and dissolved. The solution was mixed on a roller mill with 200 g hypochlorite-bleached activated charcoal (Mallinckrodt activated charcoal powder) for 30 minutes to remove organic contaminants such as polyphenols. The activated charcoal was then removed by centrifugation for 30 minutes. The resulting solution was sequentially filtered through filter paper, a 0.45 micron filter, a 0.22 micron filter and a 0.1 micron filter. 30 g sodium chloride were then added to the filtered solution and dissolved by rolling on a roller mill. The alginate was precipitated from solution by the addition of 5 L neat ethanol. The sample was centrifuged for 30 minutes to obtain an alginate pellet and the alginate pellet was suspended in ethanol and then teased apart with tweezers to insure complete washing of the sample. Excess ethanol was removed by squeezing and pressing the precipitate. The resulting precipitate was dried in an oven, under vacuum, at 60° C.

These alginates were then used for coating pancreatic islets, employing the spinning disc encapsulation apparatus of the present invention.

EXAMPLE 3

Preparation of Pancreatic Islet Suspension

This example illustrates the preparation of islets in an alginate suspension.

Pancreatic islets were isolated from dog by collagenase digestion using the method of Warnock G L, Kneteman N M, Evans M G, et al., *Can. J. Surg.*, 33:368 (1990). The final suspension of 37,000 isolated islets in 50 ml tissue culture medium (GIBCO CMRL-1066 with 25 mM HEPES, 10% Hy Clone FBS, 2 mM L-glutamine, 100μ penicillin/ml, 100 μg streptomycin/ml) was gravity sedimented at room temperature for 15 minutes. The medium was diluted 1:2 with isotonic saline by removing 25 ml medium and replacing it with 25 ml saline. The 15 minute gravity sedimentation was repeated. The supernatant was removed to 5 ml. The islets were transferred to a 15 ml conical centrifuge tube (Corning 430055) and diluted 1:3 by the addition of 10 ml saline. After a 10 minute gravity sedimentation, the supernatant was removed and the islets resuspended in 15 ml saline. The supernatant was removed to a final volume of 0.2 ml islets in saline. 0.05 ml of 3.44% sodium citrate dihydrate with 10 mM HEPES and 2.25 ml 1% high guluronate alginate (Example 1) was added to the islet suspension giving a final concentration of 14,000 islets in 0.9% alginate in saline with 10 mM HEPES and 6 mM citrate. Note: The final suspension of islets can range from 10,000–35,000 islets/ml of 0.7–1.0% alginate.

Pancreatic islets were isolated from 10 rats using the method by Lacy P E, Koztianvosky M. in *Diabetes,* 16:35 (1967). The 5,000 islets in 50 ml CMRL tissue culture medium were gravity sedimented at room temperature and washed with saline as for the dog above. The final supernatant was removed to 0.375 ml of islets in saline. 0.075 ml citrate and 1.05 ml 1% high guluronate alginate was added to the islet suspension giving a final concentration of 3,000 rat islets per ml of 0.7% alginate in saline with 10 mM HEPES and 6 mM citrate.

These pancreatic islet suspensions are then coated employing the spinning disc encapsulation apparatus of the present invention.

EXAMPLE 4

Process for Formation of First Coating

This example illustrates the process of forming the first calcium alginate coating of cell and tissue transplants.

The 14,000 dog islets suspended in 2.5 ml 0.9% high guluronate alginate prepared by the procedure of Example 3 were removed from the 15 ml centrifuge tube to a 3 ml plastic syringe by using a 16 g 2¼ inch i.v. catheter (Jelco 4062) with the needle removed. The catheter was then replaced with a 20 g blunt needle.

Using a DC electrostatic voltage of 8 KV (provided by a van de Graaff generator) between needle tip and grounded 0.117 M aqueous calcium chloride solution at ambient temperature, a suspension of pancreatic islets (14 dog islets per μl) prepared by the procedure of Example 2 was passed through a 20 gauge needle at a flow rate of approximately 200 μl/min. The suspension emerged from the needle as a thin, attenuated stream which transformed into droplets, the droplets being collected in a 60 mM petri dish (Flacon 1007) containing 10 ml calcium chloride solution. The droplets were gelled by reaction with the calcium ions in the solution. The calcium alginate coatings on the islets were smooth and uniform and had an approximate thickness of about 130 μm. The total coated particles had an average diameter of about 360 μm. This process was repeated with a suspension of 14 rat islets/μl prepared by the procedure of Example 3.

A single first coating can also be applied using the spinning disc encapsulation apparatus according to the present invention, and collecting the spheres in 100 mls of 0.120 Molar of calcium chloride.

EXAMPLE 5

Process for Preparation of Multiple Coated Pancreatic Islets Transplants with Calcium Alginate This example illustrates the process for preparation of multiple coated dog pancreatic islets transplants using an extension of the calcium alginate cross-linking.

The islets were prepared according to Example 3 and coated according to Example 4. The single coated islets in spheres were divided into two samples of 1 ml spheres per 50 ml centrifuge tube (Corning 25339-50) in the calcium chloride collecting solution. The concentration of the calcium chloride was reduced from 120 mM to 24 mM by adding 40 ml sucrose water to 10 ml of calcium chloride solution containing the 1 ml spheres. After room temperature gravity sedimentation, all fluid was removed from the spheres. To 1 ml of spheres, 1.5 ml sucrose water was added quickly followed by 8 ml 4% high mannuronate alginate solution (Example 2) while vortexing. The mixture was rotated in the mixing tube for at least 2 minutes to allow a halo to be formed. The outer coat was formed by using a spinning disc droplet generator, collecting the spheres in about 100 ml calcium chloride solution.

The spheres were gravity sedimented in three 50 ml centrifuge tubes. Each supernatant was removed to 15 ml so that all three could be combined into one 50 ml tube. After another gravity sedimentation, the supernatant was reduced to 15 ml, including 7.5 ml spheres, and 35 ml saline added for a dilution of 1:3. After sedimentation, the process was repeated, making a 1:10 dilution by adding 40 mls of saline to 10 mls of the solution containing the spheres. The final calcium concentration was 4–6 mM.

EXAMPLE 6

Process for Preparation of Multiple Coated Pancreatic Islet Transplants with Barium Cross-linked Alginate This example illustrates the process for preparation of multiple coated pancreatic islet transplants with barium cross-linked alginate halo.

The islets were prepared according to Example 3 and coated according to Example 4.

Excess calcium was removed from 1 ml spheres containing the islets by gravity sedimentation, removal of the supernatant, and resuspension in 15 ml sucrose water three times. Two ml 100 mM barium chloride with 10 mM HEPES was added to 10 ml sucrose water containing the spheres to reach a final concentration of 14 mM barium chloride. The sample was rotated for 5 minutes at room temperature. Excess barium was removed by washing 3 times with sucrose water as above. The supernatant was reduced to 1 ml and 3 ml 4% high mannuronate alginate (Example 2) was vortexed into the sample. The outer coat was formed by using a spinning disk encapsulation apparatus according to the present invention, and collecting the spheres in calcium chloride solution. The calcium chloride was diluted to 4–6 mM by washing with saline as in Example 5.

EXAMPLE 7

Process for Preparation of Multiple Coated Pancreatic Islets Transplants with Strontium Cross-linked Alginate This example illustrates the process for preparation of multiple coated pancreatic islets transplants with strontium cross-linked alginate.

The islets were prepared according to Example 3 and primary coated according to Example 4.

Soluble calcium was removed from 0.5 ml spheres containing islets by gravity sedimentation, removal of the supernatant, and resuspension in 15 ml sucrose water, repeated three times. Two ml 120 mM strontium chloride with 10 mM HEPES was added to 8 ml sucrose water containing the spheres to reach a final concentration of 24 mM. The sample was rotated for 15 minutes at room temperature using the spin disc encapsulation apparatus of the present invention. Excess strontium was removed by washing three times with sucrose waster as above.

All fluid was removed from the 0.5 ml spheres to which was added 1 ml sugar water and 2 ml 4% high mannuronate alginate (Example 2) with gentle mixing. The outer coat was formed by using the spinning disc encapsulation apparatus according to the present invention, and collecting the spheres in 10 ml calcium chloride solution. The calcium chloride was diluted to 4–6 mM by washing with saline as in Example 5.

EXAMPLE 8

Transplantation of Pancreatic Islets Coated with Multiple Coating into Diabetic Mice This example illustrates the procedure used for testing the efficacy of the coated pancreatic islets in producing and delivering insulin in diabetic mice.

Host BALB/c mice were rendered diabetic by IP injection of streptozotocin (250 mg streptozotocin/kg body weight) in 0.1 M citrate buffer, pH 4.5 several days prior to transplant. Coated islets prepared by the procedure of Example 5 were injected into the mice using a 16 g needle and a 3 ml syringe. Each animal received 0.2–2.0 ml spheres containing 500–2000 islets. Nine animals receiving multiple coated dog islets remained euglycemic from 54 days to 180 days. Three animals receiving double coated rat islets remained euglycemic from 63 days to 300$^+$ days.

Empty alginate spheres were prepared at the same time and injected i.p. into three diabetic mice. Blood glucose levels remained at 350–500 mg/dL. The mice were sacrificed at intervals and the spheres examined and found to be free from fibrosis or overgrowth by macrophages.

EXAMPLE 9

Transplantation of Pancreatic Islets Coated with Multiple Coating into Diabetic Dog This example illustrates the procedure used for testing the efficacy of the coated pancreatic islets in producing and delivering insulin in diabetic dogs.

A dog was made diabetic by total pancreatectomy. Following surgery her blood glucose level was elevated to 242 mg/dL and she required 5–7 U of NPH insulin to keep it below 250 mg/dL. The animal was transplanted while under a general anesthesia. A 14 gauge angiocatheter was inserted midline into the peritoneal cavity of the dog. After removing the needle, the multiple coated islets were injected through the catheter from a 60 ml syringe. Each syringe contained 10 ml spheres in 50 ml Dulbecco's Medium.

The dog was transplanted with 94,000 multiple coated islets 8 days post pancreatectomy, 154,000 multiple coated islets 3 days later, and 54,000 double coated islets 6 days after that for a total of 300,000 islets. There were an average of 2,300 islets/ml spheres. After transplantation, the dogs' blood glucose levels were monitored several times each day. The dog was maintained on an average of 4.5 U insulin/day for two weeks post transplant. The insulin was reduced 0.5 U every two days for the next 20 days and then the dog was removed entirely from insulin therapy. The dog has remained euglycemic for 2 years to date.

EXAMPLE 10

Multiple Coating of Calcitonin Secreting Cells

This example illustrates a multiple layer coating of calcitonin secreting cells.

A suspension of calcitonin secreting cell lines MXH-5 ($2.5 \times 10^6$) were coated with alginate according to Examples 1, 2, and 4. The second coating was applied according to Example 6, using barium chloride and the spin disc encapsulation apparatus according to the present invention.

After the second coating was applied, coated capsules were tested for viability, and cell functionality by using trypan blue dry exclusion and by alamar Blue assay.

The size of these double coated capsules was determined to be within 50–199 $\mu$m (~68%) About 50% of the coated cells were viable and functional. They were able to secrete over 200 pg/ml of calcitonin which was about 50% of the amount secreted by neat uncoated cells in culture.

Other cells isolated in cell culture are coated in the same manner.

EXAMPLE 11

Multiple Coating of Hepatocytes

This example illustrates coating of isolated hepatocytes.

Hepatocytes are isolated in a manner similar to the isolation of pancreatic cells described in Example 3. The hepatocytes are then coated according to procedure described in Examples 4, 5, 6 or 7.

After the second coating is applied, the size of the coated cells is determined and the viability and functionality of the coated cells are tested.

While particular embodiments of the present invention have been disclosed, it is to be understood that various different embodiments are possible and are contemplated within the scope of the specification, drawings, abstract and appended claims.

What is claimed is:

1. A spin disk encapsulation apparatus for forming microencapsulated transplant containing biological tissue coated by a polymer, the apparatus comprising in combination:
   a) suspension supply system comprising one or more centrally or off-center positioned needles supplying a tissue and a polymer suspension, said needles of the suspension supply system being positioned centrally or off-center of said spinning means;
   b) spinning disc or cup for forming beads comprising tissue particles and polymer suspension and for projecting them centrifugally outward, said spinning disk or cup being adjustably rotatable at a preselected first rotational speed; and
   c) one or more collection basins adapted for substantially surrounding said spinning disk or cup, being adjustably rotatable at a preselected second rotational speed, said basins being positioned relative to said spinning disk or cup to collect said beads projected from said spinning disk or cup, said first and second rotational speeds being selected so as to minimize the impact of said beads against a capture solution in said one or more collection basins.

2. The encapsulation apparatus according to claim 1, wherein said spinning disk or cup is cup shaped for receiving a suspension from the suspension supply system.

3. The encapsulation apparatus according to claim 2, wherein said cup extends into a generally diverging conically shaped sidewall, and the suspension supply system comprises at least one needle.

4. The encapsulation apparatus according to claim 3, wherein the needle of the suspension supply system is positioned off-center.

5. The encapsulation apparatus according to claim 3 comprising two or more concentrically positioned needles.

6. The encapsulation apparatus according to claim 5 wherein the needles are positioned off-center.

7. The encapsulation apparatus according to claim 4, wherein said cup shaped spinning means and said one or more collection basins having the same or different sizes are rotated in the same direction, such that said rotational speed of said one or more collection basins relative to said cup shaped spinning disk or cup minimizes the impact of said droplets against said capture solution in said one or more collection basins.

8. The encapsulation apparatus according to claim 7, wherein at least one of said one or more collection basins includes a lateral gelation chamber which is positioned to capture said droplets propelled from said cup shaped spinning means; and
   wherein when said at least one or more collection basins is rotated, said capture solution therein is propelled into said lateral gelation chamber for capturing said droplets.

9. The encapsulation apparatus according to claim 8, wherein said conically shaped sidewall includes an inner surface, and wherein said inner surface is smooth or textured for altering the thickness of the coating.

10. The encapsulation apparatus according to claim 9, wherein said mixing chamber includes a substantially cylindrical sidewall which forms a diverging angle of less than 5° with a rotational axis of said spinning means, and
    wherein said conically shaped sidewall forms an angle with said rotational axis of said spinning means, and wherein said angle is less than 90 degrees.

11. The encapsulation apparatus according to claim 6, wherein said cup shaped spinning means and said one or more collection basins having the same or different sizes are rotated in the same direction, such that said rotational speed of said one or more collection basins relative to said cup shaped spinning means minimizes the impact of said droplets against said capture solution in said one or more collection basins.

12. The encapsulation apparatus according to claim 11, wherein at least one of said one or more collection basins includes a lateral gelation chamber which is positioned to capture said droplets propelled from said cup shaped spinning means; and
    wherein when said at least one or more collection basins is rotated, said capture solution therein is propelled into said lateral gelation chamber for capturing said droplets.

13. The encapsulation apparatus according to claim 12, wherein said conically shaped sidewall includes an inner surface, and wherein said inner surface is smooth or textured for altering the thickness of the coating.

14. The encapsulation apparatus according to claim 13, wherein said mixing chamber includes a substantially cylindrical sidewall which forms a diverging angle of less than 5° with a rotational axis of said spinning means, and wherein said conically shaped sidewall forms an angle with said rotational axis of said spinning means, and wherein said angle is less than 90 degrees.

15. An encapsulation method for forming coated microcapsules containing tissue for transplantation by using a spin disk encapsulation apparatus, said method comprising:

a) preparing a suspension of a tissue in a polymer and placing it into a suspension supply system comprising a syringe and a needle;

b) introducing the suspension of step a) into a spinning cup;

c) rotating the spinning cup at a speed from about 1,000 rpm to about 30,000 rpm;

d) detecting concurrently with rotating of step c) the distance for the needle of the supply system necessary to produce a polymer coating of thickness between 20–200$\mu$;

e) setting-up said distance;

f) rotating the spinning cup at speed determined in step d) to generate droplets of the suspension traveling outward into the gelation chamber comprising a gelling solution; and g) collecting the gelled microcapsules.

16. The encapsulation method according to claim 15, wherein resulting microcapsules have a continuous and uniform coating of between 20 and 200$\mu$.

17. The encapsulation method according to claim 16, wherein resulting microcapsules have a continuous and uniform coating of between 20 and 150$\mu$.

18. The encapsulation method according to claim 15, wherein resulting microcapsules have a single continuous and uniform polymer coating of about between 20 and 200$\mu$.

19. The encapsulation method according to claim 16, wherein resulting microcapsules have a multiple continuous and uniform polymer coating of about between 20 and 200$\mu$.

* * * * *

UNITED STATES PATENT AND TRADEMARK OFFICE
Certificate

Patent No. 6,001,387                                                        Patented: December 14, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kent C. Cochrum, Davis, CA; and Randel E. Dorian, San Diego, CA.

Signed and Sealed this Twenty-eighth Day of February 2006.

THURMAN K. PAGE
*Supervisory Patent Examiner*
Art Unit 1615